US006903043B2

(12) United States Patent
Kim et al.

(10) Patent No.: US 6,903,043 B2
(45) Date of Patent: Jun. 7, 2005

(54) CHIRAL POLYMERIC SALEN CATALYST, AND A PROCESS FOR PREPARING CHIRAL COMPOUNDS FROM RACEMIC EPOXIDES BY USING THEM

(75) Inventors: Geon-Joong Kim, Seoul (KR); Dae-Woon Park, Seoul (KR); Ho Seong Lee, Daejeon (KR); Seong Jin Kim, Daejeon (KR)

(73) Assignee: Rstech Co., Ltd., Daejeon (KR)

( * ) Notice: Subject to any disclaimer, the term of this patent is extended or adjusted under 35 U.S.C. 154(b) by 0 days.

(21) Appl. No.: 10/450,643

(22) PCT Filed: Dec. 7, 2001

(86) PCT No.: PCT/KR01/02120

§ 371 (c)(1),
(2), (4) Date: Jun. 16, 2003

(87) PCT Pub. No.: WO02/48162

PCT Pub. Date: Jun. 20, 2002

(65) Prior Publication Data

US 2004/0054201 A1 Mar. 18, 2004

(30) Foreign Application Priority Data

Dec. 15, 2000 (KR) ........................................ 2000-77308

(51) Int. Cl.$^7$ ................................................ B01J 31/00
(52) U.S. Cl. ........................... 502/162; 502/165; 544/64
(58) Field of Search ........................... 544/64; 502/162, 502/165

(56) References Cited

U.S. PATENT DOCUMENTS

| | | | |
|---|---|---|---|
| 4,408,063 A | 10/1983 | Baldwin et al. | |
| 5,071,868 A | 12/1991 | Leinert | |
| 5,637,739 A | 6/1997 | Jacobsen et al. | |
| 5,663,393 A | 9/1997 | Jacobsen et al. | |
| 5,665,890 A | 9/1997 | Jacobsen et al. | |
| 5,929,232 A | 7/1999 | Jacobsen et al. | |
| 6,639,087 B2 * | 10/2003 | Larrow et al. ............... | 549/541 |

FOREIGN PATENT DOCUMENTS

| | | |
|---|---|---|
| EP | 0 431 970 B1 | 6/1991 |
| JP | 07-145157 | 6/1995 |
| JP | 2000-302772 | 10/2000 |
| WO | WO 91/14694 | 10/1991 |
| WO | WO 00/09463 | 2/2000 |

OTHER PUBLICATIONS

Seiichi Takano, et al., "Practical Synthesis of (R)–γ–Amino–β–Hydroxybutanoic Acid (GABOB) from (R)—Epichlorohydrin," Tetrahedron Letters, vol. 28, No. 16, pp. 1783–1784 (1987).

D. Scott Coffey, et al., "Preparation of (3S)–N,N–1, 7–Bis–tert–butoxycarbonyl–3–hydroxyspermidine in High Enantiomeric Purity," J. Org. Chem., vol. 64. No. 23, pp. 8741–8742 (1999).

J.J. Baldwin, et al., "Synthesis of (R)–and (S)–Epichlorohydrin," J. Org. Chem., vol. 43, No. 25, pp. 4876–4878 (1978).

Akihiro Orita, et al., "Distannoxane–Catalyzed Selective Acetylation of 3–Chloropropane–1,2–diol: A Convenient Synthesis of Enantiopure Epichlorohydrin," Synlett, No. 12, pp. 1927–1929 (1999).

Makoto Tokunaga, et al., "Asymmetric Catalysis with Water: Efficient Kinetic Resolution of Terminal Epoxides by Means of Catalytic Hydrolysis," Science, vol. 277, pp. 936–938 (Aug. 15, 1997).

C.S. Marvel and N. Tarköy, "Heat Stability Studies on Chelates from Schiff Bases of Salicylaldehyde Derivatives," JACS, vol. 79, pp. 6000–6002 (1957).

Kristien B.M. Janssen, et al., "A Dimeric Form of Jacobsen's Catalyst for Improved Retention in a Polydimethylsiloxane Membrane," Tetrahedron: Asymmetry, vol. 8, No. 20, pp. 3481–3487 (1997).

Xiaoquan Yao, et al., "Enantioselective epoxidation of Olefins Catalyzed by Two Novel Chiral Poly–salen–Mn (III) Complexes," Tetrahedron Letters, vol. 41, pp. 10267–10271 (2000).

* cited by examiner

*Primary Examiner*—Rita Desai
*Assistant Examiner*—Robert Shiao
(74) *Attorney, Agent, or Firm*—Finnegan, Henderson, Farabow, Garrett & Dunner, LLP

(57) ABSTRACT

The present invention relates to chiral salen catalysts and a process for preparing chiral compounds from racemic epoxides by using them. More particularly, the present invention is to provide a chiral polymeric salen catalyst and its use for producing chiral compounds such as chiral epoxides and chiral 1,2-diols economically in high yield and high optical purity by performing stereoselective hydrolysis or racemic epoxides.

10 Claims, 3 Drawing Sheets

CHIRAL POLYMERIC SALEN CATALYST, AND A PROCESS FOR PREPARING CHIRAL COMPOUNDS FROM RACEMIC EPOXIDES BY USING THEM

FIELD OF THE INVENTION

The present invention relates to chiral polymeric salen catalysts and a process for preparing chiral compounds from racemic epoxides by using them. More particularly, the present invention is to provide chiral polymeric salen catalysts continuously usable without any activating process of used catalyst because it does not loose a catalytic activity during the reaction process, and their use for producing chiral compounds such as chiral epoxides and chiral 1,2-diols economically in high yield and high optical purity by performing stereoselective hydrolysis of racemic epoxides.

BACKGROUND OF THE INVENTION

Chiral expoxides or chiral 1,2-diols have been widely used to prepare pharmaceuticals and agriculture products having optical properties (U.S. Pat. No. 5,071,868; *Tetrahedron Lett.*, Vol. 28, No. 16, 1783, 1987; *J. Org. Chem.*, Vol. 64, 8741, 1999). Even if these chiral epoxides or chiral 1,2-diols having high optical purity are very useful industrially, use of these compounds has been restricted because the preparation of such compounds is too difficult to produce in a large scale with low manufacturing price.

A preparation method of chiral epichlohydrins as one of chiral expoxides is disclosed using microorganism in EP 431,970 and JP 90-257895 and 94-211822. However, it is not recommended because the productivity is low and it requires two-step process. Another preparation method of chiral epichlohydrins from chiral sulfonyloxyhaloalcohol derivatives obtained from mannitol derivatives is disclosed in U.S. Pat. No. 4,408,063; and *J. Org. chem.*, Vol 43, 4876, 1978. Another preparation method of chiral epichlohydrins from 3-chloro-1,2-propanediol is also disclosed in *Syn. Lett* No. 12, 1927, 1999. However, these processes are required multi-step syntheses, so that they are also deficient to use for the industrial purpose.

Methods for preparing chiral expoxides generally use a chiral catalyst having stereoselectivity which hydrolyzes stereoselectively only one isomer from racemic epoxides mixed 50 and 50 of each isomer and leaves the un-hydrolyzed isomer in the reaction medium. However, the chiral catalyst used for said stereoselective hydrolysis is usually expensive. Therefore, if it cannot be re-used, it becomes difficult to use for the industrial purpose.

Stereoselective hydrolyses of chiral epoxides using chiral salen catalyst as a chiral catalyst are recently disclosed in *Science*, Vol. 277, 936, 1997; U.S. Pat. Nos. 5,665,890 and 5,929,232; and WO00/09463 and WO91/14694. It has been reported that the use of chiral salen catalyst provides higher yield with higher optical purity compared to uses of other chiral catalysts. However, it is reported that after hydrolysis of a racemic epoxide using conventional chiral salen catalyst, the product chiral epoxide is racemized as time goes in pages 86–87 of WO00/09463. When this hydrolysis is performed for mass production, the racemization of the product becomes deepened since it takes longer to perform the distillation to obtain the desired product, thus resulting in decrease of optical purity of the chiral epoxide. Therefore, the use of chiral salen catalyst in the production of chiral epoxides is limited for the above-mentioned reasons.

Further, when conventional chiral salen catalysts are reused, it requires an activation process after each use because activities thereof are rapidly decreased. Even if the catalyst is activated after used, the optical activity of the product prepared by using reused catalyst is remarkably lower than that of the product prepared by using fresh catalyst. Thus, there is limited to reuse. Such problems increase the manufacturing price of producing chiral epoxides.

Consequently, demand to produce chiral compounds such as chiral epoxides or chiral 1,2-diols efficiently and economically has been highly increased with the importance of such compounds to prepare pharmaceuticals and agriculture products.

SUMMARY OF THE INVENTION

The present invention has been completed by developing novel chiral polymeric salen catalyst comprising a center metal and its counterions of $PF_6^-$ or $BF_4^-$ to prevent from losing activities of chiral catalysts and racemization of chiral products because conventional chiral salen catalysts having acetate group (OAc) lose their activities or functional groups such as acetate groups thereof.

In other words, it is important to select appropriate counterions bonded to the center metal in chiral salen catalysts used in stereoselective hydrolyses of racemic epoxides. For example, chiral catalysts having nucleophilic groups such as acetate and halogen group as counterions deteriorate optical purity of products and counterions bonded weakly to the center metal in chiral catalysts can be dissociated during the reaction process, resulting in diminished catalytic activity.

The chiral polymeric salen catalyst of the present invention not only keeps its activity but also provides excellent production of chiral epoxides without racemization by comprising a center metal and counterions of $PF_6^-$ or $BF_4^-$. Further, when the chiral polymeric salen catalyst of the present invention is used in stereoselective hydrolysis of racemic epoxides, it may be easily recovered from the reaction mixture by simple filtration because it is insoluble polymer in solvent.

Therefore, an object of the present invention is to provide chiral polymeric salen catalysts which keep excellent catalytic activity after used, thus simplifying the manufacturing process since it does not require activation process of the used catalyst.

Another object of the present invention is to provide an economical process for preparing chiral epoxides and chiral 1,2-diols from racemic epoxides by using said chiral polymeric salen catalyst in high yield and high optical purity since it does not contribute for racemization of produced products.

DETAILED DESCRIPTION OF THE INVENTION

Figure 1:
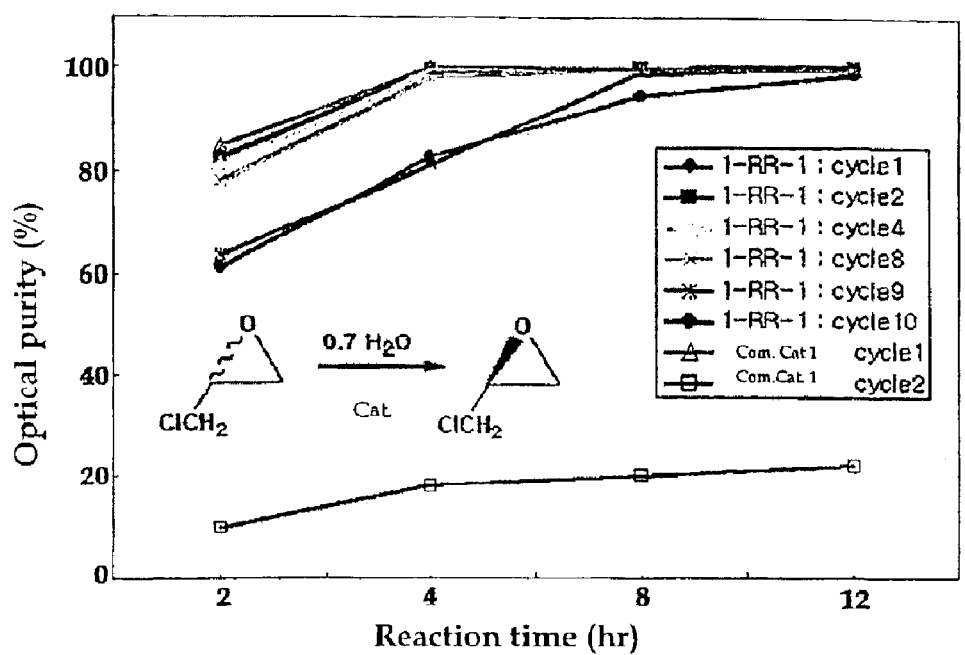
FIG. 1 represents a graph comparing an optical purity of products produced by using conventional chiral salen catalyst having acetate group with that using the chiral polymeric salen catalyst of the present invention over reaction time.

The present invention provides chiral salen catalysts expressed by the following formula (1) suitable in preparation of chiral epoxides or chiral 1,2-diols from racemic epoxides, each other to represent carbocycle or heterocycle containing 4 to 10 atoms; M represents a metal atom chosen from Co, Cr, V, Fe, Mo, W, and Ru; Z represents $PF_6$, or $BF_4$; m is an integer of 8 to 20, and n is an integer of 1 to 6.

In the stereoselective hydrolysis of racemic epoxides to chiral epoxides or chiral 1,2-diols, the present invention performs in the presence of said chiral polymeric salen catalyst of formula (1).

The present invention is described in detail as set forth hereunder. The present invention relates to the chiral polymeric salen catalyst of formula (1) and the process for preparing optically pure epoxides or 1,2-diols from racemic epoxides by stereoselective hydrolysis in the presence of the

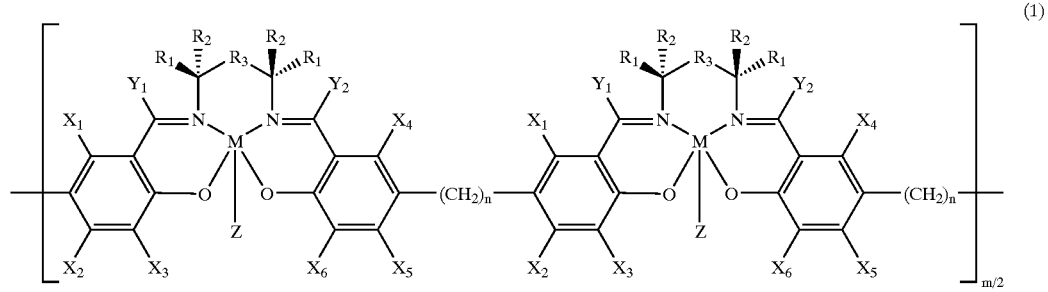

(1)

wherein $R_1$, $R_2$, $R_3$, $X_1$, $X_2$, $X_3$, $X_4$, $X_5$, $X_6$, $Y_1$, and $Y_2$ represent individually a hydrogen atom, $C_1$–$C_6$ alkyl, $C_2$–$C_6$ alkenyl, $C_2$–$C_6$ alkynyl, halogen, hydroxy, amino, thiol, nitro, amine, amide, carbonyl, carboxyl, silyl, ether, thioether, salenoether, ketone, aldehyde, ester, phosphoryl, phosphonate, phosphine, sulfonyl, or $(CH_2)_k$-$R_4$, where $R_4$ is phenyl, cycloalkyl, cycloalkenyl, heterocycle or polycycle and k is an integer of 0 to 8, or any of two can be bonded chiral polymeric salen catalyst which can be reused continuously without an activation process after used and does not affect racemization of the produced products.

The chiral polymeric salen catalyst of formula (1) can be prepared by reacting phenol derivative of formula (2) with diamine derivative of formula (3) to obtain a compound of formula (4) and introducing a center metal and counterions as described in Scheme 1, Scheme 1

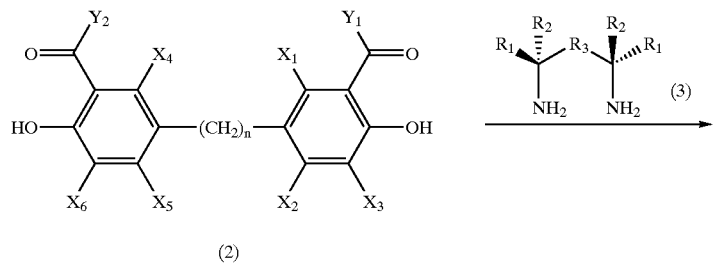

(2)

(3)

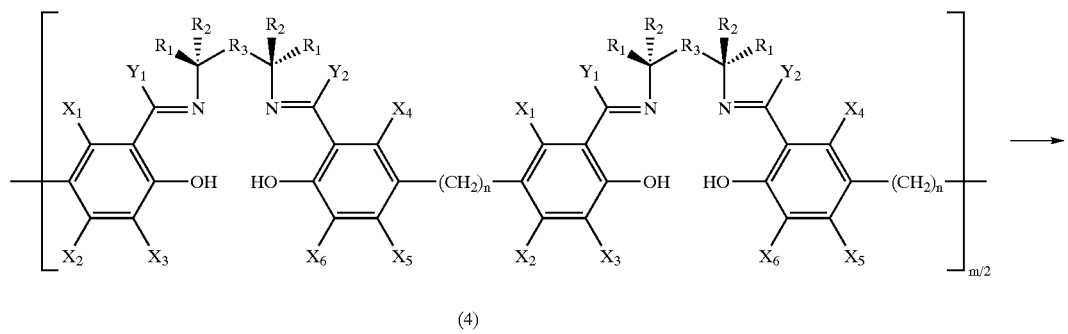

(4)

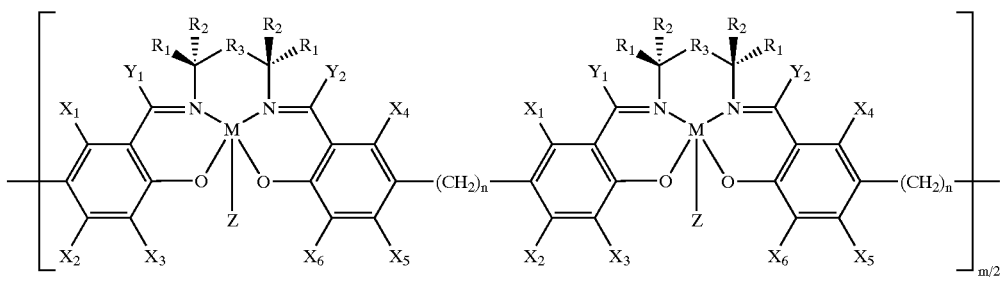

(1)

wherein $R_1$, $R_2$, $R_3$, $X_1$, $X_2$, $X_3$, $X_4$, $X_5$, $X_6$, $Y_1$, $Y_2$, M, Z, n and m are same as previously defined.

The polymeric salen ligand of formula (4) in Scheme 1 may be prepared by known methods in *J. Am. Chem. Soc., Vol.* 79, 6000, 1957; *Tetrahedron: Asymmetry, Vol.* 8, No. 20, pp. 3481–3487, 1997; and *Tetrahedron Letters, Vol.* 41, pp. 10267–10271, 2000. The reaction of phenol derivative of formula (2) with diamine derivative of formula (3) is performed at 0° C. to 150° C. A solvent used in the reaction may be an alcohol such as methanol, ethanol, and propanol, dichloromethane, chloroform, or dichloroethane. The reaction is performed for at least 2 hours to obtain enough polymerization. The produced polymeric salen ligand of formula (4) is filtered, washed with water, ethanol, and hexane and dried. A center metal (M) is introduced to the polymeric salen ligand of formula (4) by reacting with a salt containing the center metal atom in an alcohol such as methanol, ethanol, propanol and the like at a temperature of 20 to 150° C. Further, counterions (Z) are introduced to produce the desired polymeric salen catalyst of formula (1) by reacting with a salt containing counterions (Z) or ferrocenium derivatives in an organic solvent methanol, ethanol, propanol, dichloromethane, chloroform, dichloroethane, acetonitrile, tetrahydrofuran, tetrahydropyran, 1,4-dioxane and the like.

The mechanism of preparing chiral epoxides or chiral 1,2-diols from racemic epoxides in the presence of the chiral polymeric salen catalyst of formula (1) by stereoselective hydrolysis is shown in Scheme 2, Scheme 2

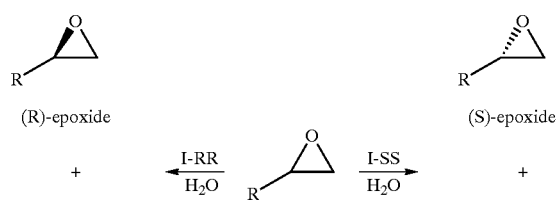

-continued

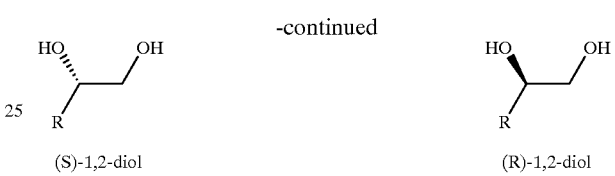

wherein R represents unsubstituted or halogen-substituted $C_1$–$C_{10}$ alkyl, unsubstituted or halogen-substituted $C_3$–$C_8$ cycloalkyl, or unsubstituted or halogen-substituted phenyl; I-RR represents a chiral polymeric salen catalyst of formula (1), where $R_1$ is a hydrogen atom; I-SS represents a chiral polymeric salen catalyst of formula (1), where $R_2$ is a hydrogen atom.

The stereoselective hydrolysis of Scheme 2 is described in more detail hereinafter. A racemic epoxide compound, 0.4–0.8 equivalents of water and over 0.001 mol % of a chiral polymeric salen catalyst, preferably 0.1–5 mol %, are reacted at a temperature of −10 to 30° C., preferably 4 to 25° C. The reaction can be performed in an organic solvent, but it is preferable to perform in the absence of any solvent. After the reaction is completed, a chiral polymeric salen catalyst is recovered by filtration and the filtrate is performed for fractional distillation to isolate chiral epoxide or chiral 1,2-diol. The recovered catalyst is re-used for hydrolysis of fresh racemic epoxide to produce chiral epoxide or chiral 1,2-diol without any activation process.

When the chiral polymeric salen catalyst of formula (1), where $R_1$ is a hydrogen atom, (hereafter referring to as "I-RR") is used for the stereoselective hydrolysis, (R)-epoxide or (S)-1,2-diol is produced, while when the chiral polymeric salen catalyst of formula (1), where $R_2$ is a hydrogen atom, (hereafter referring to as "I-SS") is used, (S)-epoxide or (R)-1,2-diol is produced.

Figure 2:
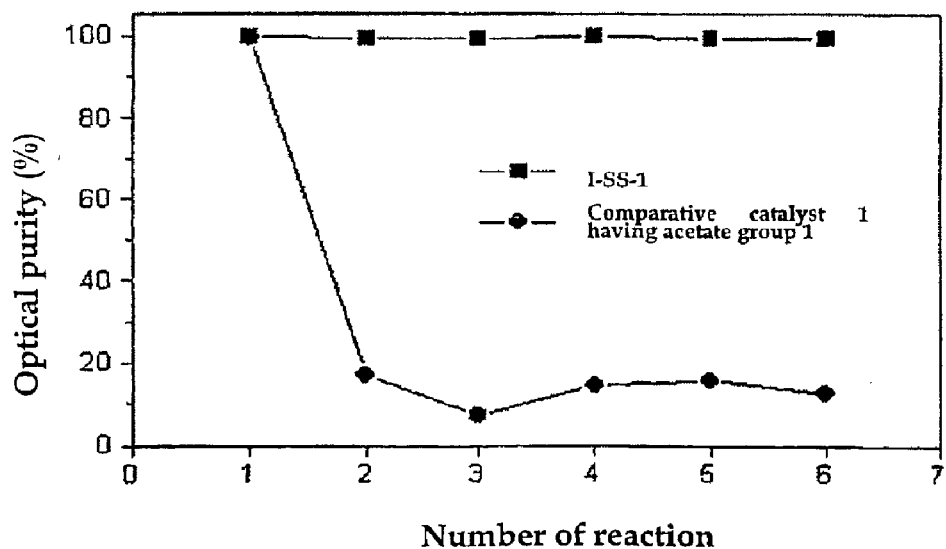
FIG. 2 represents a graph comparing an optical purity of products produced by using conventional chiral salen catalyst having acetate group with that using the chiral polymeric salen catalyst of the present invention over number of times it is used.

FIGS. 1 and 2 are graphs comparing a reaction rate and stereoselectivity of conventional chiral polymeric salen catalyst having acetate group (comparative catalyst 1) with those of chiral polymeric salen catalyst (I-RR-1 or I-SS-1) of the present invention over reaction time.

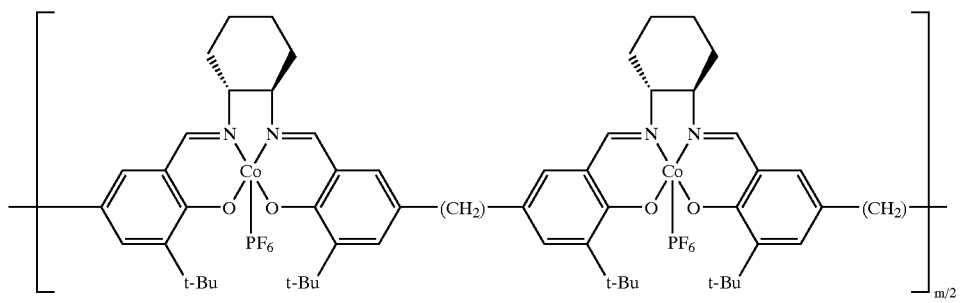

I-RR-1 catalyst

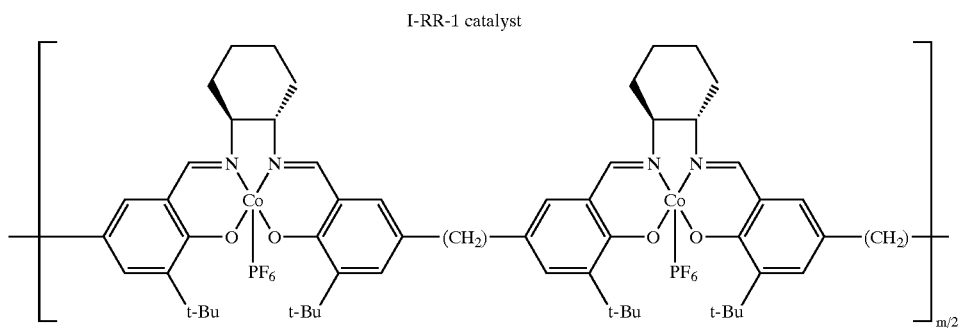

I-SS-1 catalyst

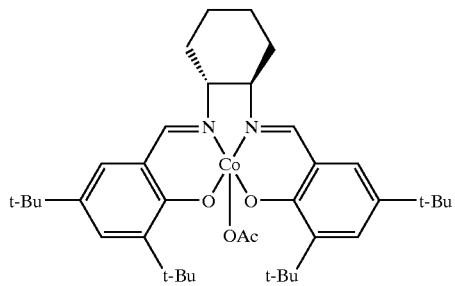

Comparative catalyst 1

In FIGS. 1 and 2, the use of the chiral polymeric salen catalyst of the present invention shows faster reaction rate and higher stereoselectivity (over 99% ee) than that of the conventional chiral salen catalyst having acetate group. It is further proved that the chiral polymeric salen catalyst of the present invention can be used continuously without any activation process, while the conventional chiral salen catalyst having acetate group has to be activated with acetic acid after each use, because it looses its catalytic activity and the reaction using recovered catalyst takes much longer to obtain over 99% ee of optical purity of the product than that using fresh catalyst.

Figure 3:
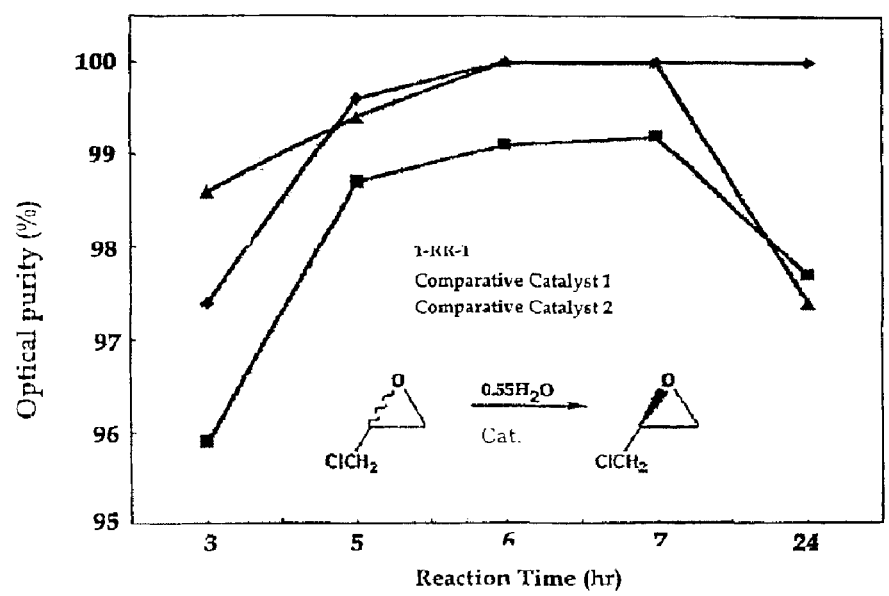
FIG. 3 represents a graph comparing degrees of racemization of products produced by using conventional chiral salen catalyst having acetate group and conventional chiral salen catalyst having bromide group with that using the chiral polymeric salen catalyst of the present invention over reaction time.

FIG. 3 represents a graph comparing degrees of racemization of products produced by using conventional chiral salen catalyst having acetate group (OAc; comparative catalyst 1) and conventional chiral salen catalyst having bromide group (Br; comparative catalyst 2) with that using the chiral polymeric salen catalyst (I-RR-1) of the present invention over reaction time.

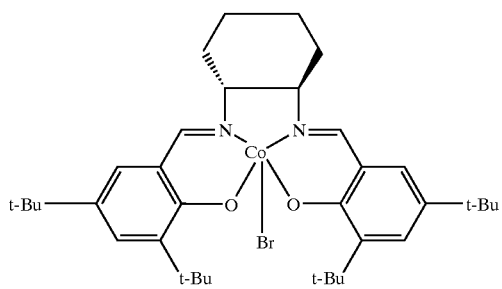

Comparative catalyst 2

In FIG. 3, when the chiral polymeric salen catalyst of the present invention is used, there is no or little of racemization over reaction of time, while when conventional chiral salen catalyst having acetate group (OAc; comparative catalyst 1) or conventional chiral salen catalyst having bromide group (Br; comparative catalyst 2) is used, the degree of racemization becomes higher over reaction time, resulting in lowering optical purity of the corresponding product because the conventional chiral salen catalysts contain counterions having a nuclophilic group. In the mass production of chiral epoxides, it will take longer reaction time to distill the desired product. Therefore, it is expected that use of the chiral polymeric salen catalyst of the present invention contributes to produce optically pure chiral epoxide, while use of the comparative catalyst 1 or 2 produces in lowered optical purity due to racemization during distillation process.

Hereunder is given the more detailed description of the present invention using examples. However, it should not be construed as limiting the scope of the present invention.

EXAMPLE 1

Preparation of (S,S)-N-(3-t-butylsalicylidene)-N'-(3-t-butyl-5-methylenesalicylidene)-1,2-cyclohexanediamine Polymer

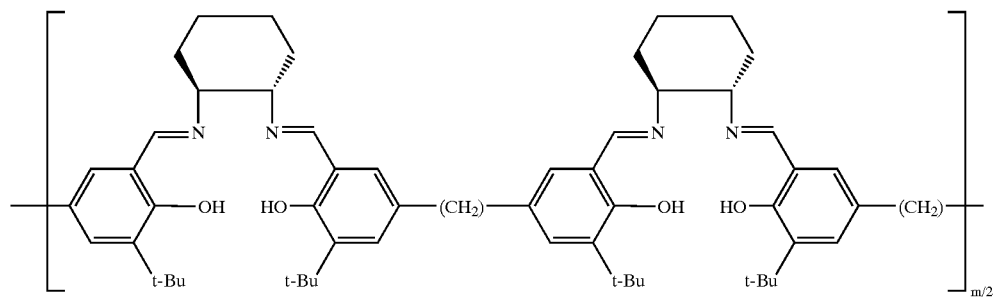

21.6 g of (S,S)-1,2-diammoniumcyclohexane mono-(−)-tartrate and 22.6 g of potassium carbonate were dissolved in 110 mL of water and 440 mL of ethanol was added thereto. 30.1 g of 5,5'-methylene-di-3-t-butylsalicyl aldehyde dissolved in 250 mL of ethanol was added at the reflux temperature. After the reaction mixture was refluxed for 12 hrs while stirring, 110 mL of water was added thereto and the temperature was come down to 5° C. The reaction mixture was filtered, washed with 220 mL of water twice, 70 mL of ethanol and 70 mL of hexane, and dried to obtain the target product (32.8 g).

IR (KBr, cm$^{-1}$): 778, 800, 860, 1160, 1265, 1440, 1594, 1628, 2860, 2960; Average molecular weight (GPC):5856 (Polydispersity=1.06)

EXAMPLE 2

Preparation of (R,R)-N-(3-t-butylsalicylidene)-N'-(3-t-butyl-5-methylenesalicylidene)-1,2-cyclohexanediamine Polymer

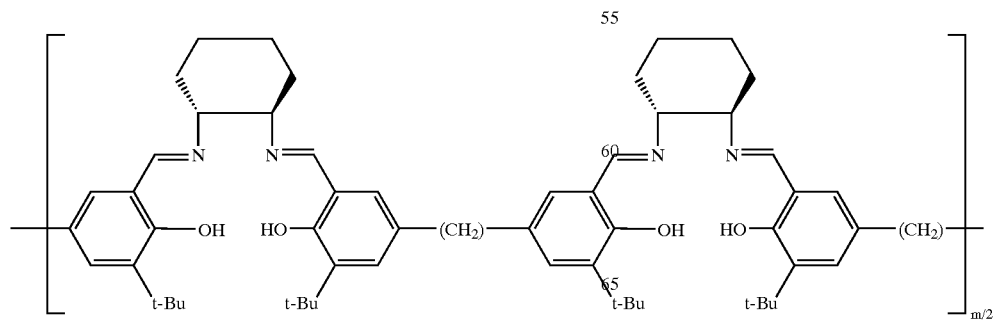

Figure 4:
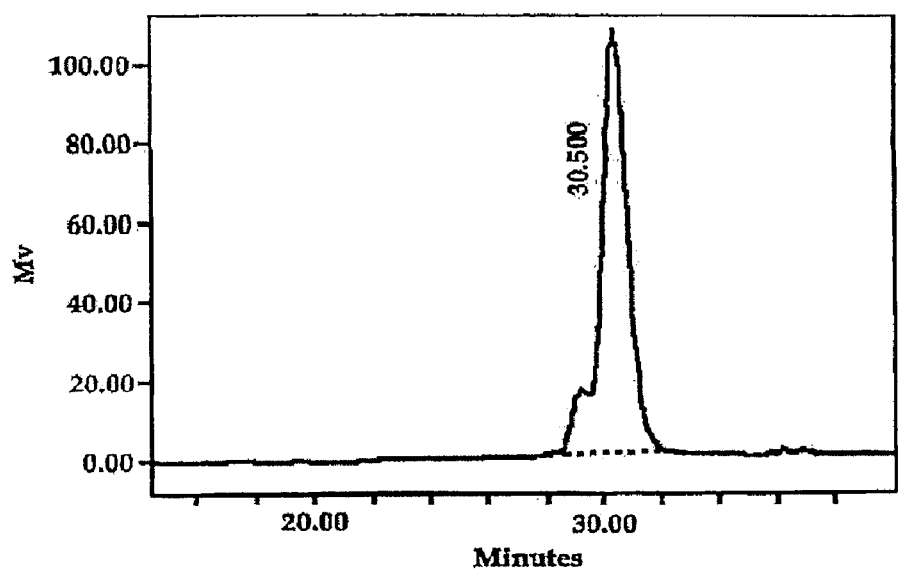
FIG. 4 represents GPC data of polymeric salen ligand used in the preparation of the chiral polymeric salen catalyst of the present invention.

The reaction was performed in the same manner as Example 1 except that (R,R)-1,2-diammoniumcyclohexane mono-(+)-tartrate was used instead of (S,S)-1,2-diammoniumcyclohexane mono-(−)-tartrate to obtain the target product (32.7 g).
IR (KBr, cm$^{-1}$):778, 800, 860, 1160, 1265, 1440, 1594, 1628, 2860, 2960; Average molecular weight (GPC, FIG. 4):5856 (Polydispersity=1.06)

EXAMPLE 3

Preparation of (S,S)-N-(3-t-butylsalicylidene)-N'-(3-t-butyl-5-methylenesalicylidene)-1,2-cyclohexanediaminocobalt(III) Hexafluorophosphate Polymer

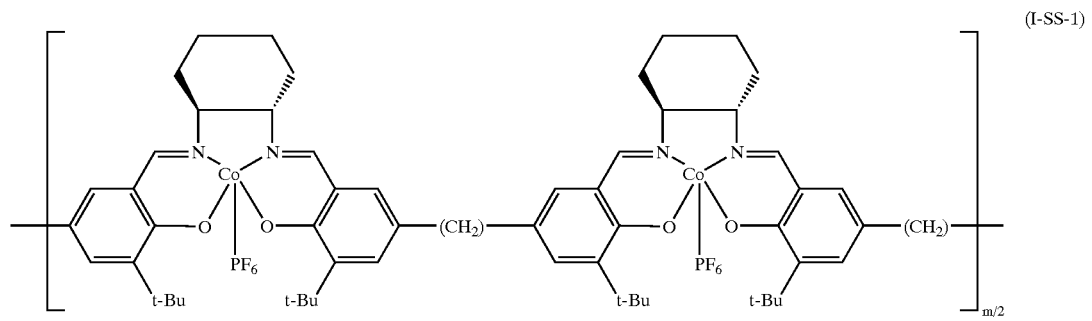

(I-SS-1)

1 Equivalent of (S,S)-N-(3-t-butylsalicylidene)-N'-(3-t-butyl-5-methylenesalicylidene)-1,2-cyclohexanediamine polymer and 1.2 equivalents of cobalt(II)acetate.4H$_2$O were added to ethanol and refluxed for 3 hrs while stirring. The reaction mixture was filtered at room temperature. The obtained solid, 1 equivalent of ferrocenium hexafluorophosphate and acetonitrile were mixed and refluxed for 1 hr while stirring. Acetonitrile was then evaporated under pressure. The residue was washed with hexane, followed by filtration to obtain the target product.
IR(cm$^{-1}$):849, 1032, 1165, 1231, 1335, 1387, 1437, 1538, 1572, 2864, 2948, 3481

EXAMPLE 4

Preparation of (R,R)-N-(3-t-butylsalicylidene)-N'-(3-t-butyl-5-methylenesalicylidene)-1,2-cyclohexanediaminocobalt(III) Hexafluorophosphate Polymer

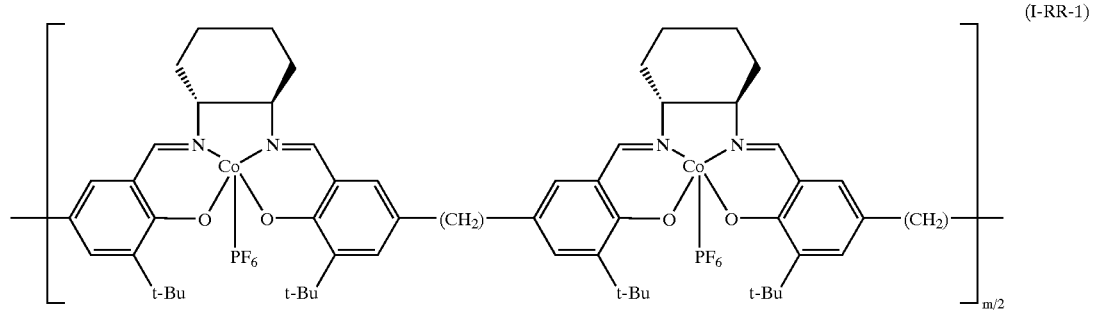

(I-RR-1)

The reaction was performed in the same manner as Example 3 except that (R,R)-N-(3-t-butylsalicylidene)-N'-(3-t-butyl-5-methylenesalicylidene)-1,2-cyclohexanediamine polymer was used instead of (S,S)-N-(3-t-butylsalicylidene)-N'-(3-t-butyl-5-methylenesalicylidene)-1,2-cyclohexanediamine polymer to obtain the target product.

IR(cm$^{-1}$):849, 1032, 1165, 1231, 1335, 1387, 1437, 1538, 1572, 2864, 2948, 3481

EXAMPLE 5

Preparation of (S,S)-N-(3-t-butylsalicylidene)-N'-(3-t-butyl-5-methylenesalicylidene)-1,2-cyclohexanediamino Cobalt(III) Tetrafluoroborate Polymer

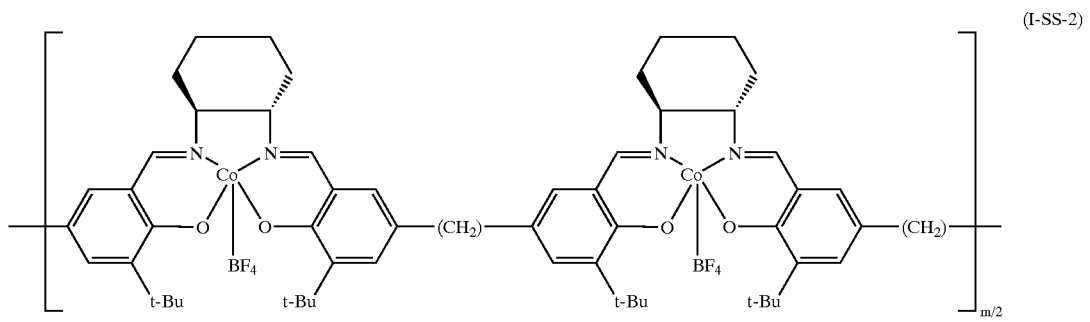

(I-SS-2)

1 Equivalent of (S,S)-N-(3-t-butylsalicylidene)-N'-(3-t-butyl-5-methylenesalicylidene)-1,2-cyclohexanediamine polymer and 1.2 equivalents of cobalt(II)acetate.4H$_2$O were added to ethanol and refluxed for 3 hrs while stirring. The reaction mixture was filtered at room temperature. The obtained solid, 1 equivalent of ferrocenium tetrafluoroborate and acetonitrile were mixed and refluxed for 1 hr while stirring. Acetonitrile was then evaporated under pressure. The residue was washed with hexane, followed by filtration to obtain the target product.

IR(cm$^{-1}$):841, 1031, 1164, 1229, 1336, 1383, 1438, 1544, 1571, 2862, 2954, 3484

EXAMPLE 6

Preparation of (R,R)-N-(3-t-butylsalicylidene)-N'-(3-t-butyl-5-methylenesalicylidene)-1,2-cyclohexanediaminocobalt(III) Tetrafluoroborate Polymer

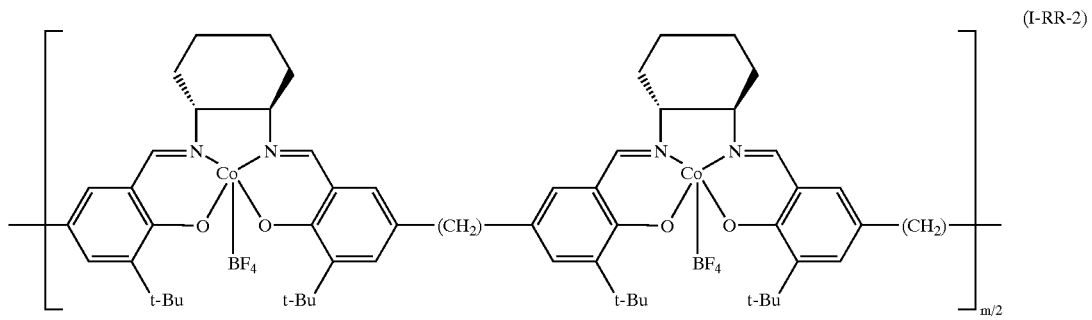

(I-RR-2)

The reaction was performed in the same manner as Example 5 except that (R,R)-N-(3-t-butylsalicylidene)-N'-(3-t-butyl-5-methylenesalicylidene)-1,2-cyclohexanediamine polymer was used instead of (S,S)-N-(3-t-butylsalicylidene)-N'-(3-t-butyl-5-methylenesalicylidene)-1,2-cyclohexanediamine polymer to obtain the target product.

IR(cm$^{-1}$):841, 1031, 1164, 1229, 1336, 1383, 1438, 1544, 1571, 2862, 2954, 3484

EXAMPLE 7

Preparation of (S,S)-N-(3-t-butylsalicylidene)-N'-(3-t-butyl-5-methylenesalicylidene)-1,2-cyclohexanediamino Cobalt(III) Bromide Polymer

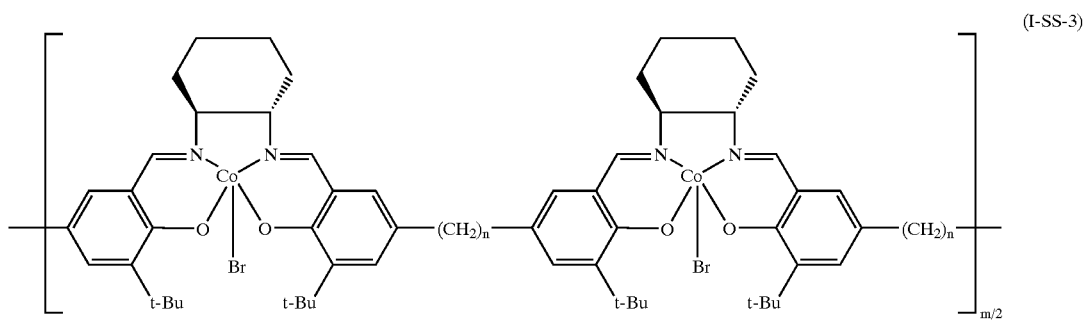

(I-SS-3)

1 Equivalent of (S,S)-N-(3-t-butylsalicylidene)-N'-(3-t-butyl-5-methylenesalicylidene)-1,2-cyclohexanediamine polymer and 1.2 equivalents of cobalt(II)acetate.4H$_2$O were added to ethanol and refluxed for 3 hrs while stirring. The reaction mixture was filtered at room temperature. The obtained solid and 0.5 equivalent of bromine were added into dichloromethane and refluxed for 1 hr while stirring. Dichloromethane was then evaporated under pressure to obtain the target product.

EXAMPLE 8

Preparation of (R,R)-N-(3-t-butylsalicylidene)-N'-(3-t-butyl-5-methylenesalicylidene)-1,2-cyclohexanediaminocobalt(III) Bromide Polymer

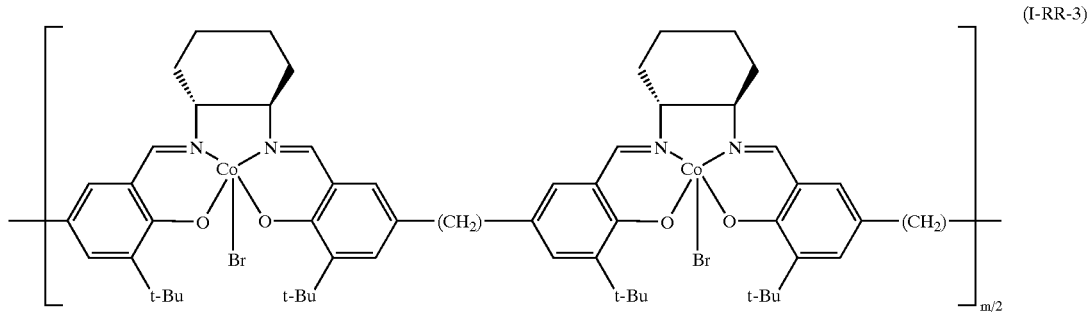

(I-RR-3)

The reaction was performed in the same manner as Example 7 except that (R,R)-N-(3-t-butylsalicylidene)-N'-(3-t-butyl-5-methylenesalicylidene)-1,2-cyclohexanediamine polymer was used instead of (S,S)-N-(3-t-butylsalicylidene)-N'-(3-t-butyl-5-methylenesalicylidene)-1,2-cyclohexanediamine polymer to obtain the target product.

EXAMPLE 9

Preparation of (S,S)-N-(3-t-butylsalicylidene)-N'-(3-t-butyl-5-methylenesalicylidene)-1,2-cyclohexanediamino Cobalt(III) Chloride Polymer

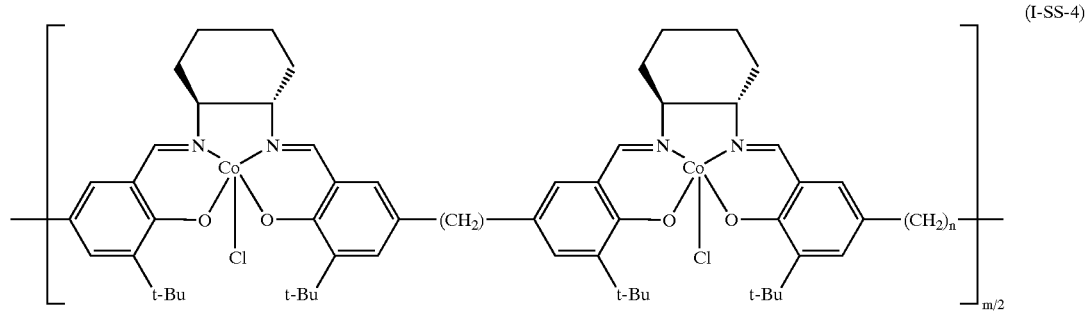

(I-SS-4)

1 Equivalent of (S,S)-N-(3-t-butylsalicylidene)-N'-(3-t-butyl-5-methylenesalicylidene)-1,2-cyclohexanediamine polymer and 1.2 equivalents of cobalt(II)acetate.4H$_2$O were added to ethanol and refluxed for 3 hrs while stirring. The reaction mixture was filtered at room temperature. The obtained solid and 0.5 equivalent of chlorine were added into dichloromethane and refluxed for 1 hr while stirring. Dichloromethane was then evaporated under pressure to obtain the target product.

EXAMPLE 10

Preparation of (R,R)-N-(3-t-butylsalicylidene)-N'-(3-t-butyl-5-methylenesalicylidene)-1,2-cyclohexanediaminocobalt(III) Chloride Polymer

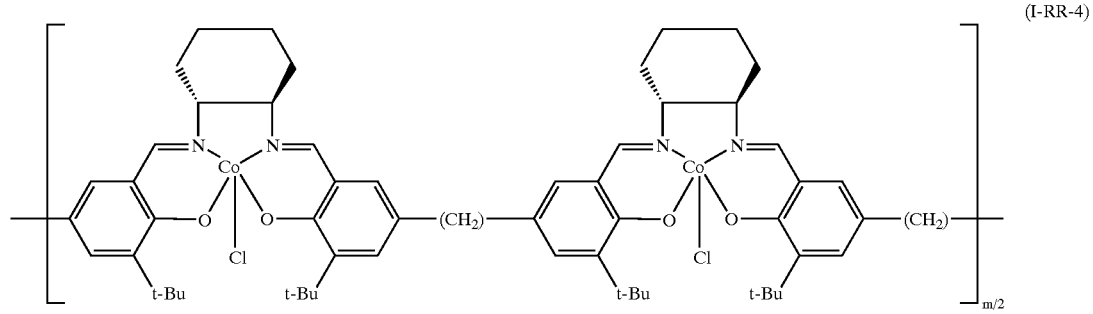

(I-RR-4)

The reaction was performed in the same manner as Example 9 except that (R,R)-N-(3-t-butylsalicylidene)-N'-(3-t-butyl-5-methylenesalicylidene)-1,2-cyclohexanediamine polymer was used instead of (S,S)-N-(3-t-butylsalicylidene)-N'-(3-t-butyl-5-methylenesalicylidene)-1,2-cyclohexanediamine polymer to obtain the target product.

EXPERIMENTAL EXAMPLE 1

Preparation of (S)-epichlorohydrin or (R)-epichlorohydrin

Each 100 g of racemic epichlorohydrin was added to 0.25 mol % of the catalysts prepared in Examples 3 to 10 and cooled to 5° C. Each 13.6 g of water was added slowly to each reaction mixture and then stirred at 20° C. for 4 hrs. Each reaction mixture was filtered to recover each catalyst and then the filtrate was performed for fractional distillation to obtain (S)[or (R)]-epichlorohydrin. The recovered catalyst without any activation process was reused for another hydrolysis reaction of racemic epichlorohydrin continuously to obtain (S)[or (R)]-epichlorohydrin with over 99% ee of optical purity.

COMPARATIVE EXPERIMENTAL EXAMPLE 1

Preparation of (S)-epichlorohydrin (S)-Epichlorohydrin was prepared in the same manner as Experimental Example 1 by using the conventional chiral salen catalyst having acetate group (comparative catalyst 1). When the used catalyst was used for next reaction without any activation process, (S)-epichlorohydrin with 17% ee of optical purity was prepared. After the second reaction, the used catalyst was activated by a known method (*Science*, Vol. 277, 936, 1997). The used catalyst was added in toluene and 2 equivalent of acetic acid and stirred for 1 hr under atmosphere condition and the solvent was then evaporated under pressure to obtain recovered catalyst. When the third reaction was performed by using the recovered catalyst, the reaction took 7 to 8 hrs under the same reaction condition to obtain (S)-epichlorohydrin with lower than 99% ee of optical purity, while it took only 4 hr when the fresh catalyst was used. The result was summarized in Table 1.

TABLE 1

| Catalyst | Nos. of reaction performed | Optical purity (% ee) | Ave. yield* | Reaction time |
|---|---|---|---|---|
| Comparative catalyst 1 having acetate group | 1st | >99.8 | 80% | 4 hr |
| | 2nd (w/o activation) | 17 | — | 8 hr |
| | 3rd (w/ activation) | <99 | 80% | 8 hr |
| I-RR-1 (or I-SS-1) | 1st | >99.8 | 80% | 4 hr |
| | 2nd | >99.8 | | 5 hr |
| | 4th | >99.8 | | 5 hr |
| | 8th | >99.5 | | 8 hr |
| I-RR-2 (or I-SS-2) | 1st | >99.8 | 80% | 4 hr |
| | 2nd | >99.8 | | 4 hr |
| | 4th | >99.7 | | 6 hr |
| | 6th | >99.4 | | 8 hr |
| I-RR-3 (or I-SS-3) | 1st | >99.8 | 80% | 2 hr |
| | 2nd | >99.7 | | 3 hr |
| | 4th | >99.6 | | 4 hr |
| | 5th | >99.4 | | 6 hr |
| I-RR-4 (or I-SS-4) | 1st | >99.8 | 78% | 2 hr |
| | 2nd | >99.8 | | 3 hr |
| | 4th | >99.5 | | 4 hr |
| | 5th | >99.1 | | 6 hr |

*Ave. yield: theoretical yield based to maximum yield 50%

COMPARATIVE EXPERIMENTAL EXAMPLE 2

Comparison in Optical Purity Changes of (S)-epichlorohydrin

Each 0.4 mol % of the catalyst I-RR-1 prepared in Example 4, comparative catalyst 1 having acetate group, and comparative catalyst 2 having bromo group was added to 100 g of racemic epichlorohydrin separately and cooled to 5° C. 10.7 g of water was slowly added to each reaction mixture of which was stirred at 20° C. The optical purity of each reaction mixture was measured over reaction time as shown in FIG. 3.

EXPERIMENTAL EXAMPLE 2

Preparation of (R)-epibromohydrin or (S)-epibromohydrin 2.8 g of the catalyst prepared in Example 3 (I-SS-1) or Example 4 (I-RR-1) was added to 148 g of racemic epibromohydrin and cooled to 5° C. 10.7 g of water was slowly added to the reaction mixture of which was stirred at 20° C. for 7 hrs. The reaction mixture was filtered to recover used catalyst and the filtrate was performed for fractional distillation under pressure to obtain (R) [or (S)]-epibromohydrin. The recovered catalyst was used for next reaction without any activation process to produce (R) [or (S)]-epibromohydrin with over 99% ee of optical purity.

EXPERIMENTAL EXAMPLE 3

Preparation of (S)-1,2-epoxybutane or (R)-1,2-epoxybutane 2.8 g of the catalyst prepared in Example 3 (I-SS-1) or Example 4 (I-RR-1) was added to 78 g of racemic 1,2-epoxybutane and cooled to 5° C. 10.7 g of water was slowly added to the reaction mixture of which was stirred at 20° C. for 7 hrs. The reaction mixture was filtered to recover used catalyst and the filtrate was performed for fractional distillation under pressure to obtain (S) [or (R)]-1,2-epoxybutane. The recovered catalyst was used for next reaction without any activation process to produce (S) [or (R)]-1,2-epoxybutane with over 99% ee of optical purity.

EXPERIMENTAL EXAMPLE 4

Preparation of (S)-1,2-epoxyhexane or (R)-1,2-epoxyhexane

The reaction was performed in the same manner as Experimental Example 3 except that 108 g of racemic 1,2-epoxyhexane was used instead of racemic 1,2-epoxybutane to obtain the target product with over 99% ee of optical purity.

EXPERIMENTAL EXAMPLE 5

Preparation of (S)-styrene Oxide or (R)-styrene Oxide 5 g of the catalyst prepared in Example 3 (I-SS-1) or Example 4 (I-RR-1) was added to 130 g of racemic styrene oxide and cooled to 5° C. 13.6 g of water was slowly added to the reaction mixture, which was stirred at 20° C. for 15 hrs. The reaction mixture was filtered to recover used catalyst and the filtrate was performed for fractional distillation under pressure to obtain first (S) [or (R)]-styrene oxide. The recovered catalyst was reused for next reaction without any activation process to produce (S) [or (R)]-styrene oxide with over 99% ee of optical purity.

EXPERIMENTAL EXAMPLE 6

Preparation of (S)-1,2-butandiol or (R)-1,2-butandiol 2.8 g of the catalyst prepared in Example 3 (I-SS-1) or Example 4 (I-RR-1) was added to 78 g of racemic 1,2-epoxybutane and cooled to 5° C. 8.8 g of water was slowly added to the reaction mixture, which was stirred at 20° C. for 3 hrs. The reaction mixture was filtered to recover used catalyst and the filtrate was performed for fractional distillation under pressure to obtain first (S) [or (R)]-1,2-butandiol. The recovered catalyst was reused for next reaction without any activation process to produce (S) [or (R)]-1,2-butandiol with over 99% ee of optical purity and average yield of 80%.

As described above, the chiral polymeric salen catalyst of the present invention can be recovered by simple filtration and reused without any activation process, which is a disadvantage associated with conventional chiral salen catalyst, and used in mass production of chiral epoxides or chiral 1,2-dials from racemic epoxides in high yield and high optical purity by stereoselective hydrolysis.

What is claimed is:

1. A chiral polymeric salen catalyst of formula (1),

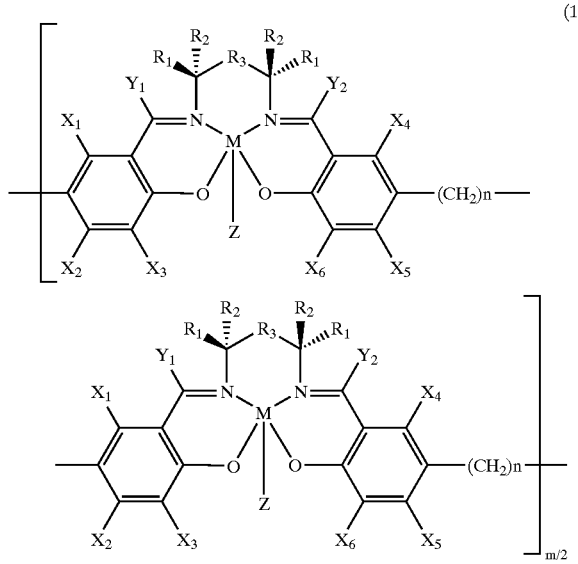

wherein $R_1$, $R_2$, $R_3$, $X_1$, $X_2$, $X_3$, $X_4$, $X_5$, $X_6$, $Y_1$, and $Y_2$ represent individually a hydrogen atom, $C_1$–$C_6$ alkyl, $C_2$–$C_6$ alkenyl, $C_2$–$C_6$ alkynyl, halogen, hydroxy, amino, thiol, nitro, amine, amide, carbonyl, carboxyl, silyl, ether, thioether, salenoether, ketone, aldehyde, ester, phosphoryl, phosphonate, phosphine, sulfonyl, or $(CH_2)_k$—$R_4$, where $R_4$ is phenyl, cycloalkyl, or cycloalkenyl,
k is an integer of 0 to 8, and
any two of $R_1$, $R_2$, or $R_3$, can be bonded to each other to form a carbocycle containing 4 to 10 atoms;

M represents a metal atom chosen from Co, Cr, V, Fe, Mo, W, and Ru;

Z represents $PF_6$, or $BF_4$;

m is an integer of 8 to 20;

n is an integer of 1 to 6; and with the proviso that $R_3$ is not a hydrogen atom, halogen, hydroxy, amino, nitro, amine or amide.

2. A chiral polymeric salen catalyst according to claim 1, wherein said $X_1$, $X_2$, $X_3$, $X_4$, $X_5$, and $X_6$ represent individually a hydrogen atom or t-butyl group; and said $Y_1$ and $Y_2$ represent individually a hydrogen atom.

3. A chiral polymeric salen catalyst according to claim 1, wherein said M is Co.

4. A chiral polymeric salen catalyst according to claim 1, wherein said n is an integer of 1.

5. A chiral polymeric salen catalyst according to claim 1, wherein said m is an integer of 10–20.

6. A method for preparing chiral polymeric salen catalyst of formula (1) comprising the following steps:

reaction of phenol derivative of formula (2) with diamine derivative of formula (3) to produce polymeric salen ligand of formula (4); and introduction of a center metal (M) and counter ions (Z) to the obtained polymeric salen catalyst of formula (1),

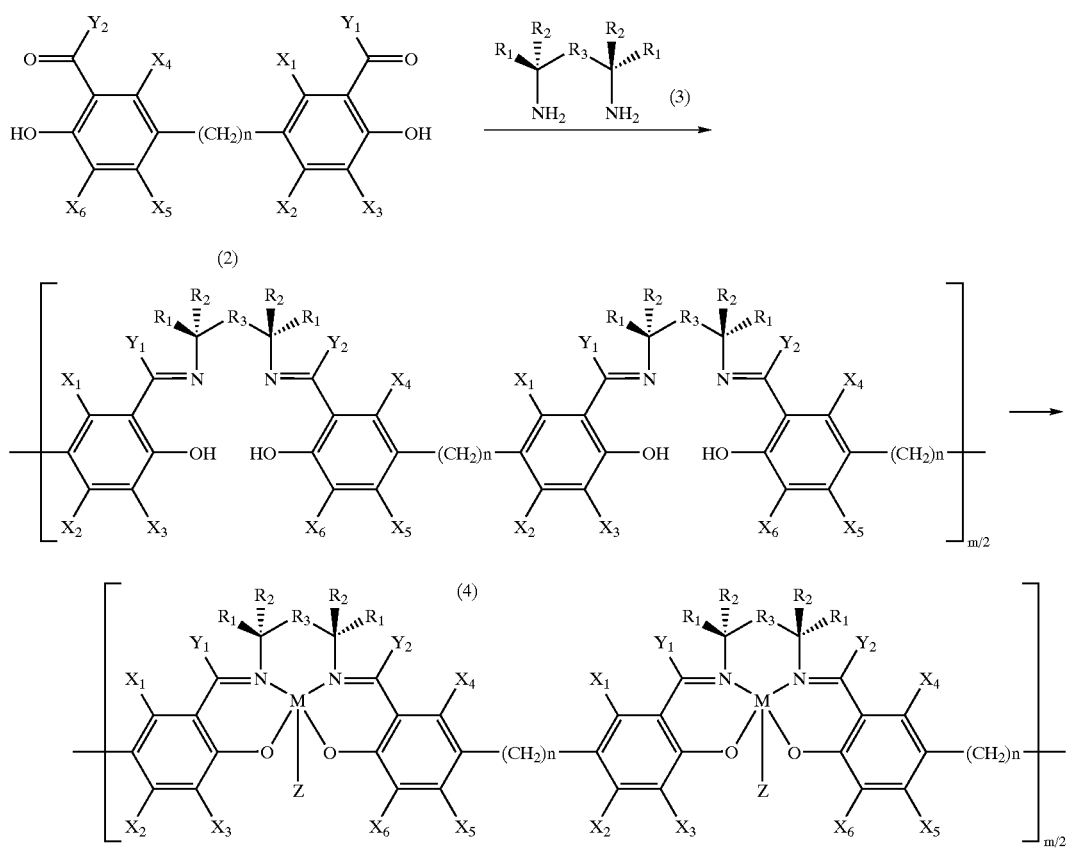

wherein $R_1$, $R_2$, $R_3$, $X_1$, $X_2$, $X_3$, $X_4$, $X_5$, $X_6$, $Y_1$, and $Y_2$ represent individually a hydrogen atom, $C_1$–$C_6$ alkyl, $C_2$–$C_6$ alkenyl, $C_2$–$C_6$ alkynyl, halogen, hydroxy, amino, thiol, nitro, amine, amide, carbonyl, carboxyl, silyl, ether, thioether, salenoether, ketone, aldehyde, ester, phosphoryl, phosphonate, phosphine, sulfonyl, or $(CH_2)_k$—$R_4$, where $R_4$ is phenyl, cycloalkyl, or cycloalkenyl,
k is an integer of 0 to 8, and
any two of $R_1$, $R_2$, or $R_3$, can be bonded to each other to form a carbocycle containing 4 to 10 atoms;

M represents a metal atom chosen from Co, Cr, V, Fe, Mo, W, and Ru;

Z represents $PF_6$, or $BF_4$;

m is an integer of 8 to 20;

n is an integer of 1 to 6; and with the proviso that $R_3$ is not a hydrogen atom, halogen, hydroxy, amino, nitro, amine or amide.

7. A method for preparing chiral polymeric salen catalyst according to claim 6, wherein said $X_1$, $X_2$, $X_3$, $X_4$, $X_5$, and $X_6$ represent individually a hydrogen atom or t-butyl group; and said $Y_1$ and $Y_2$ represent individually a hydrogen atom.

8. A method for preparing chiral polymeric salen catalyst according to claim 6, wherein said M is Co.

9. A method for preparing chiral polymeric salen catalyst according to claim 6, wherein said n is an integer of 1.

10. A method for preparing chiral polymeric salen catalyst according to claim 6, wherein said m is an integer of 10–20.

* * * * *